(12) United States Patent
Jain et al.

(10) Patent No.: US 12,094,571 B2
(45) Date of Patent: Sep. 17, 2024

(54) SYSTEMS AND METHODS FOR PREDICTIVE MOLECULAR BIOMARKER IDENTIFICATION AND QUANTIFICATION FROM MORPHOLOGY CHANGES IN HISTOPATHOLOGY TISSUE

(71) Applicant: DHRISTI INC., Saratoga, CA (US)

(72) Inventors: Parag Jain, Palo Alto, CA (US); Rajat Roy, Saratoga, CA (US); Bijay Shankar Jaiswal, San Mateo, CA (US)

(73) Assignee: PATHOMIQ INC., Saratoga, CA (US)

(*) Notice: Subject to any disclaimer, the term of this patent is extended or adjusted under 35 U.S.C. 154(b) by 886 days.

(21) Appl. No.: 17/174,310

(22) Filed: Feb. 11, 2021

(65) Prior Publication Data
US 2021/0249101 A1    Aug. 12, 2021

Related U.S. Application Data

(60) Provisional application No. 62/975,172, filed on Feb. 11, 2020.

(51) Int. Cl.
*G06N 5/04*       (2023.01)
*G06N 20/00*      (2019.01)
(Continued)

(52) U.S. Cl.
CPC .............. *G16B 20/20* (2019.02); *G06N 5/04* (2013.01); *G06N 20/00* (2019.01); *G06T 7/0012* (2013.01);
(Continued)

(58) Field of Classification Search
CPC .............................. G16H 50/20; G16H 30/20
See application file for complete search history.

(56) References Cited

U.S. PATENT DOCUMENTS 10,395,772 B1    8/2019  Lucas
2006/0234235 A1*  10/2006  Harris ................. C12Q 1/6886
                                                              435/6.18
(Continued)

FOREIGN PATENT DOCUMENTS

WO        2019/219651 A1    11/2019

OTHER PUBLICATIONS

Yue, Xingzhi, Neofytos Dimitriou, and Ognjen Arandjelovic. "Colorectal cancer outcome prediction from H&E whole slide images using machine learning and automatically inferred phenotype profiles." arXiv preprint arXiv:1902.03582 (2019). (Year: 2019).*
Mobadersany, Pooya, et al. "Predicting cancer outcomes from histology and genomics using convolutional networks." Proceedings of the National Academy of Sciences 115.13 (2018): E2970-E2979. (Year: 2018).*
(Continued)

*Primary Examiner* — Hal Schnee
(74) *Attorney, Agent, or Firm* — Cognition IP, P.C.; Edward Steakley

(57) ABSTRACT

Methods and systems for identifying and quantifying molecular biomarkers and for predicting patient response to cancer therapy are provided. The disclosed methods and systems make use of artificial intelligence to capture morphometric changes from histopathology tissue that correlate with molecular changes. The system may analyze molecular markers which are predictive of tumor response and have no defined correlation with morphological features. The system may use artificial intelligence to correlate morphometric changes with critical gene modifications and molecular changes.

22 Claims, 13 Drawing Sheets

(51) Int. Cl.
  G06T 7/00     (2017.01)
  G06T 7/11     (2017.01)
  G16B 20/10    (2019.01)
  G16B 20/20    (2019.01)
  G16B 40/30    (2019.01)
  G16H 10/40    (2018.01)
  G16H 30/40    (2018.01)
  G16H 50/20    (2018.01)
  A61B 10/00    (2006.01)

(52) U.S. Cl.
  CPC ............... G06T 7/11 (2017.01); G16B 20/10 (2019.02); G16B 40/30 (2019.02); G16H 10/40 (2018.01); G16H 30/40 (2018.01); G16H 50/20 (2018.01); A61B 10/0041 (2013.01); G06T 2207/20081 (2013.01); G06T 2207/30024 (2013.01); G06T 2207/30096 (2013.01); G06T 2207/30204 (2013.01)

(56) References Cited

U.S. PATENT DOCUMENTS

| | | | |
|---|---|---|---|
| 2009/0275057 A1* | 11/2009 | Linke | G01N 33/57419 |
| | | | 435/7.23 |
| 2010/0184093 A1 | 7/2010 | Donovan et al. | |
| 2015/0301058 A1 | 10/2015 | Schettini et al. | |
| 2016/0125130 A1* | 5/2016 | Le Cocq | G16B 30/00 |
| | | | 702/19 |
| 2017/0275701 A1 | 9/2017 | Garcia | |
| 2020/0250817 A1* | 8/2020 | Leng | G01N 33/57434 |
| 2020/0365268 A1* | 11/2020 | Michuda | G16H 50/20 |
| 2021/0271847 A1* | 9/2021 | Courtiol | G06V 20/698 |

OTHER PUBLICATIONS

International Search Report in PCT International Application No. PCT/US2021/017730, mailed Apr. 30, 2021.
Extended European Search Report received in European application No. 21753062.5, mailed Nov. 7, 2023.

* cited by examiner

| Mutation/ Copy Number Variation (CNV) | Total no of patients (N) | Mutation/ CNV Positive (Outcome 1) | Mutation/ CNV Negative (Outcome 0) | ROC AUC Score |
|---|---|---|---|---|
| PTEN loss * | 385 | 85 | 300 | 73% |
| TMPRSS2-ERG fusion * | 390 | 155 | 235 | 70% |
| TP53 mutation ** | 742 | 292 (39%) | 450 | 80% |
| PIK3CA mutation ** | 742 | 228 (31%) | 514 | 74% |
| MYC amplification ** | 742 | 101 (13%) | 618 | 77% |
| ERBB2 amplification ** | 719 | 98 (14%) | 621 | 78% |

\* Prostate Cancer (PCa)
\*\* Breast Invasive Ductal Carcinoma (IDC)

| Antibody information | | | | |
|---|---|---|---|---|
| Antibody | Vendor | Cat# | clone | dilution |
| CD4 | Ventana | #790-4423 | Rabbit mAb | Pre-diluted |
| CD8 | Ventana | #790-4460 | Rabbit mAb | Pre-diluted |
| CD20 | Ventana | #760-2531 | Mouse mAb | Pre-diluted |
| CD57 | Ventana | #790-2626 | Mouse mAb | Pre-diluted |
| CD68 | Ventana | #790-2931 | Mouse mAb | Pre-diluted |
| CD163 | Ventana | #760-4437 | Mouse mAb | Pre-diluted |
| AR | Cell Signaling | #9559 | Rabbit mAb | Pre-diluted |
| CC3 | Cell Signaling | #9579 | Rabbit mAb | 1:50 |
| CTLA-4 | Abcam | #ab227709 | Rabbit mAb | 1:100 |
| CD74 | Abcam | #ab64772 | Rabbit pAb | 1:320 |
| Ki67 | Ventana | #790-4286 | Rabbit mAb | Pre-diluted |
| PD-L1 | Abcam | #ab205921 | Rabbit mAb | 1:100 |
| PSA | Ventana | #760-4271 | Mouse mAb | Pre-diluted |
| PSMA | Cell Marque | #760-6076 | Rabbit mAb | Pre-diluted |
| pTEN | Cell signaling | #9559 | Rabbit mAb | 1:200 |
| TMEM | Abcam | #ab205921 | Rabbit mAb | 1:4000 |

FIG. 8

| 4-1BB | CD40 | EPCAM | IL15 | STAT1 |
| AKT1 | CD40LG | FAS | ITGAV | STAT2 |
| ARG1 | CD44 | FOXP3 | ITGB2 | STAT3 |
| B2M | CD45 | GZMB | ITGB8 | TBX21 |
| B7-H3 | CD47 | HIF1A | KI67 | TIGIT |
| BATF3 | CD68 | HLA-DQA1 | LAG3 | Tim3 |
| BCL2 | CD74 | HLA-DRB1 | LY6K | TNF |
| CCL5 | CD80 | HLA-E | Muc-1K | VEGFA |
| CCND1 | CD86 | ICAM1 | NKG7 | VISTA |
| CD3E | CSF1R | ICOSLG | pan-Melanoma | OX40 |
| CD4 | CTLA4 | IDO1 | PD-1 | PDL1A |
| CD8A | CTNNB1 | IFNAR1 | PD-L1 | XAF1 |
| CD11b | CXCL9 | IFNG | PD-L2 | SOX4 |
| CD11c | CXCL10 | IFNGR1 | PECAM1 | LGR |
| CD20 | CXCR | IL6 | PSMB10 | |
| CD27 | SKK2 | IL2R | PTEN | |

Table: Protein/RNA Panel

FIG. 9

| Samples N = 20 | Red ROIs | Yellow ROIs | Red ROIs | Yellow ROIs | Red ROIs | Yellow ROIs | Red ROIs | Yellow ROIs |
|---|---|---|---|---|---|---|---|---|
| | % KI67 | | % CC3 | | % TMEM | | % PDL1 | |
| Median | | 4.61 | | 1.56 | | 0.99 | | 10.83 |
| Mean | | 6.11 | | 3.9 | | 3.09 | | 15.79 |
| Std Dev | | 5.18 | | 5.54 | | 5.37 | | 17.67 |
| p-value | 0.00195 | | 0.05381 | | 0.01773 | | 0.00978 | |

| Samples N = 20 | Red ROIs | Yellow ROIs | Red ROIs | Yellow ROIs | Red ROIs | Yellow ROIs | Red ROIs | Yellow ROIs |
|---|---|---|---|---|---|---|---|---|
| | OD TMEM | | OD PTEN | | CD8 Density | | CD163 Density | |
| Median | | 0.16 | | 0.21 | | 176 | | 91 |
| Mean | | 0.18 | | 0.21 | | 230 | | 193 |
| Std Dev | | 0.09 | | 0.08 | | 214 | | 258 |
| p-value | 0.08667 | | 0.06397 | | 0.00394 | | 0.00278 | |

| Samples N = 20 | Pca | Periphery | Pca | Periphery | Pca | Periphery | Pca | Periphery |
|---|---|---|---|---|---|---|---|---|
| | CD8 Density | | CD163 Density | | CD68 Density | | CD20 Density | |
| Median | 204 | 92 | 167 | 82 | 331 | 152 | 136 | 67 |
| Mean | 280 | 113 | 183 | 108 | 339 | 182 | 167 | 73 |
| Std Dev | 208 | 86 | 162 | 99 | 205 | 91 | 156 | 61 |
| p-value | 0.00060 | | 0.00163 | | 0.03463 | | 0.00321 | |

Table: Biomarker Panel for tumor progression prediction

FIG. 10

| Samples N = 20 | Red ROIs | Yellow ROIs | Red ROIs | Yellow ROIs | Red ROIs | Yellow ROIs | Red ROIs | Yellow ROIs |
|---|---|---|---|---|---|---|---|---|
| | % Ki67 | | % CC3 | | % TMEM | | % PDL1 | |
| Median | | 4.61 | | 1.56 | | 0.99 | | 10.83 |
| Mean | | 6.11 | | | | 3.09 | | 15.79 |
| Std Dev | | 5.18 | | 5.54 | | 5.37 | | 17.67 |
| p-value | 0.00195 | | 0.05381 | | 0.01773 | | 0.00978 | |

| Samples N = 20 | Red ROIs | Yellow ROIs | Red ROIs | Yellow ROIs | Red ROIs | Yellow ROIs | Red ROIs | Yellow ROIs |
|---|---|---|---|---|---|---|---|---|
| | OD TMEM | | OD PTEN | | CD8 Density | | CD163 Density | |
| Median | | 0.16 | | 0.21 | | 176 | | 91 |
| Mean | | 0.18 | | 0.21 | | 230 | | 193 |
| Std Dev | | 0.09 | | 0.08 | | 214 | | 258 |
| p-value | 0.08667 | | 0.06397 | | 0.00394 | | 0.00228 | |

| Samples N = 20 | Pca | Periphery | Pca | Periphery | Pca | Periphery | Pca | Periphery |
|---|---|---|---|---|---|---|---|---|
| | CD8 Density | | CD163 Density | | CD68 Density | | CD20 Density | |
| Median | 204 | 92 | 167 | 82 | 231 | 152 | 124 | 67 |
| Mean | 260 | 113 | 183 | 108 | 239 | 182 | 167 | 73 |
| Std Dev | 208 | 86 | 162 | 99 | 155 | 93 | 159 | 61 |
| p-value | 0.00060 | | 0.00163 | | 0.03463 | | 0.00321 | |

Table: Multivariate Analysis

FIG. 13

| | Slope | Standard Error | p-value |
|---|---|---|---|
| Intercept | 5.17 | 0.42 | |
| 1:%Ki67(p=0.00195) | 1.43 | 0.57 | 0.0388 |
| 2:%CC3(p=0.05381) | -0.54 | 0.16 | 0.0106 |
| 3:%TMEM(p=0.01773) | -1.20 | 0.40 | 0.0204 |
| 4:%PDL1(p=0.00978) | 1.66 | 0.48 | 0.0103 |
| 5:OD-TMEM(p=0.08667) | 1.64 | 0.52 | 0.0156 |
| 6:OD-PTEN(p=0.06397) | -3.53 | 0.84 | 0.0039 |
| 7:CD8-Density(p=0.0394) | -0.77 | 0.34 | 0.0581 |
| 8:CD8-Density(p=0.00060) | 2.41 | 0.48 | 0.0016 |
| 9:CD163-Density(p=0.00163) | -2.55 | 0.58 | 0.0031 |
| 10:CD68-Density(p=0.03463) | 1.98 | 0.64 | 0.0174 |

FIG. 14

SYSTEMS AND METHODS FOR PREDICTIVE MOLECULAR BIOMARKER IDENTIFICATION AND QUANTIFICATION FROM MORPHOLOGY CHANGES IN HISTOPATHOLOGY TISSUE

CROSS-REFERENCE TO RELATED APPLICATIONS

This application claims the benefit of U.S. Provisional Application 62/975,172, filed Feb. 11, 2020, which is hereby incorporated by reference in its entirety.

FIELD OF THE INVENTION

This invention relates generally to molecular biomarker identification and quantification for predicting patient response to cancer therapy, and in particular to the use of artificial intelligence to capture morphometric changes from histopathology tissue that correlate with molecular changes.

BACKGROUND

Identification of molecular biomarkers is useful for prognosis and prediction of treatment response and to make informed decisions regarding treatment tailored to the needs of an individual subject. In personalized medicine, molecular diagnostic testing is used to identify the best course of treatment for an individual subject, wherein the best course of treatment consists in identifying the best drug for the individual, and predicting optimal drug dosage that is safe and efficacious for the subject, and how long the subject's response to the drug lasts or time to relapse. Molecular diagnostic/predictive tests involve detection and/or analysis of a molecular biomarker in a subject to identify clinically relevant information about the subject.

Current techniques to discover biomarkers that predict patient response are focused on single or a set of biochemical markers and the structured molecular data of those markers, such as DNA, RNA, and protein data. Thus far, genomic based single biomarkers have been predictive of therapy response in a minority of cases, such as in epidermal growth factor receptor (EGFR), rat sarcoma viral oncogene homolog (RAS), and anaplastic lymphoma kinase (ALK) mutations in lung cancer. Additional biomarkers for disease outcome include select complex proteomic/genomic patterns comprised of several proteins found in subjects with cancer, which are not found in healthy individuals. However, in a majority of cases, a single analyte or even a set of proteogenomic biomarkers cannot provide sufficient information regarding complex arrays of cellular physiological processes that drive disease and treatment outcome. Systems and methods that can distinguish responders from non-responders to cancer therapy with higher accuracy are warranted. Such systems will help select the right treatment for individual subjects at different disease states for the majority of cases where no single genomic biomarker is driving tumor progression.

Current techniques aimed at discovering biomarkers that predict patient response are focused on structured molecular data, such as genomic and proteomic information. Molecular analyses are performed at a whole tissue level that delivers an average molecular signature across tens of thousands of cancers, benign and micro-environmental (stroma, immune etc.) cells. These techniques work when a single or few genes are heavily over-expressed in cancer and/or its microenvironment. However, tumors are inherently heterogeneous and there are several molecular subtypes with varying levels of expression in a tissue sample. In many cases, <1% of the cancer cells may be the most aggressive and informative of molecular pathways of the disease progression and thus, of the patient outcome. This molecular signal gets lost when averaged over the entire tissue.

Also, tumor alone does not capture the full picture—it is the spatial interaction of the tumor with the Tumor Micro-Environment (TME) that includes stroma, several types of immune cells, blood vessels etc., whose interplay determines tumor aggressiveness and patient response to a particular therapy. Current proteogenomic analyses are not suited to capture the TME dynamics, there is no single RNA or protein that is driving patient response and outcome.

Histopathology as observed through Hematoxylin and Eosin (H&E) stained slides is currently used for cancer diagnosis. However, there are distinct morphological changes in the way the tumor cells organize themselves and these patterns evolve as the cells undergo molecular changes. These molecular changes such as gene mutations, copy number variations, gene fusions etc. in many cases result in morphological changes. However, it is not known what these changes are, and hence pathologists in standard-of-care are unable to discern which pattern or patterns are indicative of such changes. Imaging may capture distinct tumor microenvironments with spatial organization of the tumor, immune, stromal and other cells, which influence patient response to therapy. Consequently, there is a need for systems and methods that can identify and extract morphometric features from histopathology slides for disease diagnosis/prognosis and therapy selection. The methods disclosed herein provide a solution to the aforementioned challenges by employing artificial intelligence (AI) in an unsupervised manner to identify and extract sought after morphologic features.

SUMMARY

Provided herein are methods and systems for predicting molecular changes in a subject's tissue, such as gene mutations, copy number variations, gene fusions directly from morphometric analysis of H&E stained tissue section images.

In one embodiment, provided herein is a method of directly predicting molecular changes in one or more tissue sections from a subject, wherein the method comprises (a) analyzing molecular markers, which are predictive of tumor response and have no defined correlation with morphological features, such that the method is carried out in unsupervised manner; and (b) using artificial intelligence to correlate morphometric changes with critical gene modifications and molecular changes.

Using artificial intelligence comprises (i) collecting whole-slide images (WSIs) of tissue sections obtained from the subject; (ii) feature extracting the whole-slide images into patches and corresponding vectors to generate clusters of vectors with morphologically similar patterns; (iii) sampling the patches uniformly across each cluster to generate a batch of vectors that represent the subject's images; (iv) generating a score between 0 and 1 for each patch based on gene status; and (v) generating an outcome morphometric score for the subject by combining selected patches.

The method comprises selecting an N×N region around each patch, and generating a mean vector for each region. In some embodiments, molecular markers include, but are not limited to, PTEN, TMPRSS2-ERG, TP53, PIK3CA, MYC and ERBB2.

Extracted features are trained on multiple tumor types. Tumor types may comprise prostate, breast, gastrointestinal, ovary, liver and lung tumors.

In some embodiments, the tissue sections are stained with hematoxylin and eosin (H&E). Molecular changes comprise one or more gene modifications selected from gene mutations, copy-number variations (CNV), gene amplifications, gene deletions and gene fusions.

A score of about 1 indicates a gene modification and a score of about 0 indicates a wild type gene.

Generating an outcome morphometric score for the subject indicates learning of predictive features. In some embodiments, the method predicts a range of gene modifications across a range of tumor types with 70 to 90% accuracy.

In some embodiments, the method further comprises identifying, collecting patches causing miss-predictions and generating training data to fine-tune predictions.

The method may further comprise identifying regions of interest on tissue sections, which are predictive of outcome.

In a different embodiment, provided herein is a system for directly predicting molecular changes in one or more tissue sections from a subject, wherein the system is configured to (a) analyze molecular markers, which are predictive of tumor response and have no defined correlation with morphological features, such that the analysis is carried out in unsupervised manner; and (b) use artificial intelligence to correlate morphometric changes with critical gene modifications and molecular changes.

To use artificial intelligence, the system is configured to (a) collect whole-slide images (WSIs) of tissue sections obtained from the subject; (b) feature extract the whole-slide images into patches and corresponding vectors to generate clusters of vectors with morphologically similar patterns; (c) sample the patches uniformly across each cluster to generate a batch of vectors that represent the subject's images; (d) generate a score between 0 and 1 for each patch based on gene status; and (e) generate an outcome morphometric score for the subject by combining selected patches.

The system is also configured to select an N×N region around each patch, and generate a mean vector for each region.

Molecular markers include, but are not limited to, PTEN, TMPRSS2-ERG, TP53, PIK3CA, MYC and ERBB2. The system may be is trained on multiple tumor types and multiple gene modifications. Tumor types may comprise prostate, breast, gastrointestinal, ovary, liver and lung tumors.

Tissue sections are stained with hematoxylin and eosin (H&E). Molecular changes comprise of one or more gene modifications selected from gene mutations, copy-number variations (CNV), gene amplifications, gene deletions and gene fusions. A score of 1 indicates a gene modification and a score of about 0 indicates an intact gene. In some embodiments, generating an outcome morphometric score for the subject forces the system to learn predictive features.

The system may predict a range of gene modifications across a range of tumor types with 70 to 90% accuracy, and it may be further configured to identify and collect patches causing miss-predictions, and generate training data to fine-tune predictions.

The system may be further configured to identify regions of interest on tissue sections, which are predictive of outcome.

In yet another embodiment, provided herein are methods and systems for directly predicting an outcome of one or more subjects having a disease or at risk of developing a disease, and for identifying regions of interest that are predictive of disease outcome in one or more tissue sections from the subjects.

The disclosed methods comprise (a) collecting whole-slide images (WSIs) of tissue sections obtained from one or more subjects; (b) identifying regions of interest (ROIs) corresponding to morphological features correlated with disease outcome; using method as described in previous patent (c) probing the ROIs with RNA probes and antibody probes; (d) identifying and quantifying RNA and proteins expressed in the ROIs; (e) performing a correlation analysis between the RNA and the proteins expressed in the ROIs; and (f) identifying biomarkers in the ROIs which are not expressed or are either more or less expressed in other areas of the tissues and in tissues from patients with favorable outcome, thereby identifying ROIs that are predictive of disease outcome and predicting the outcome of the one or more subjects.

The tissue sections are stained with hematoxylin and eosin (H&E). The method may further comprise identifying mechanisms or pathways for therapy response specific to biomarker expression in the ROIs. The ROIs comprise cancer regions, stromal regions and regions that contain immune cells.

The biomarkers comprise of but are not limited to biomarkers specific for cytotoxic T cells, B cells, macrophages, M1 macrophages, cancer stem cells and MHC class II. In some embodiments, the biomarkers comprise of but are not limited to Ki67, CC3, AR, PTEN, PD-L1, PD-1, CD57, CD8, CD4, CD3, CD20, CD68, CD163, CD44, CD45, HLA-DR, CD74 STING pathway such as TMEM and several others that may be over-expressed or under-expressed in the ROIs.

The method may further comprise determining spatial distribution of identified biomarkers in tumor microenvironments by immunohistochemical (IHC), immunofluorescence (IF) analysis, CyTOF, MALDI-TOF and other protein detection and estimation methods in whole tissue and tissue sections.

The method may further comprise combining quantitative biomarker expression in the ROIs with morphological data of the ROIs by co-registering IHC and/or IF whole slide tissue sections with hematoxylin and eosin (H&E) whole slide tissue sections to increase accuracy of prediction.

The disclosed systems are configured to (a) collect whole-slide images (WSIs) of tissue sections obtained from one or more subjects; (b) identify regions of interest (ROIs) corresponding to morphological features correlated with disease outcome; using method described in previous patent and (c) probe the ROIs with RNA probes and antibody probes; (d) identify and quantify RNA and proteins expressed in the ROIs; (e) perform a correlation analysis between the RNA and the proteins expressed in the ROIs; and (f) identify biomarkers in the ROIs which are not expressed or are more or less expressed in other areas of the tissues and in tissues from patients with favorable outcome, thereby identifying ROIs that are predictive of disease outcome and predicting the outcome of the one or more subjects.

The tissue sections are stained with hematoxylin and eosin (H&E). The system may be further configured to identify mechanisms or pathways for therapy response specific to biomarker expression in the ROIs. The ROIs comprise cancer regions, stromal regions and regions that contain immune cells.

The biomarkers comprise of but are not limited to biomarkers specific for cytotoxic T cells, B cells, macrophages, M1 macrophages, cancer stem cells and MHC class II. In some embodiments, the biomarkers comprise of but are not limited to Ki67, CC3, AR, PTEN, PD-L1, PD-1, CTLA-4, CD57, CD8, CD4, CD3, CD20, CD68, CD163, CD44, CD45, HLA-DR, CD74 and STING Pathway proteins such as TMEM and several others that may be over-expressed or under-expressed in the ROI.

The system may be further configured to determine spatial distribution of identified biomarkers in tumor microenvironments by immunohistochemical (IHC) and/or immunofluorescence (IF) analysis on whole slide tissue sections.

The system may be further configured to combine quantitative biomarker expression in the ROIs with morphological data of the ROIs by co-registering IHC and/or IF whole slide tissue sections with hematoxylin and eosin (H&E) whole slide tissue sections to increase accuracy of prediction.

BRIEF DESCRIPTION OF THE DRAWINGS

The present disclosure will become better understood from the detailed description and the drawings, wherein:

FIG. 8 illustrates an example table describing Antibody information.

FIG. 9 illustrates an example table describing a protein/RNA panel.

FIG. 10 illustrates an example table describing a biomarker panel for tumor progression prediction.

FIG. 13 illustrates an example table describing a multivariate analysis FIG. 14 illustrates an example table showing statistical analysis.

DETAILED DESCRIPTION

Figure 1:
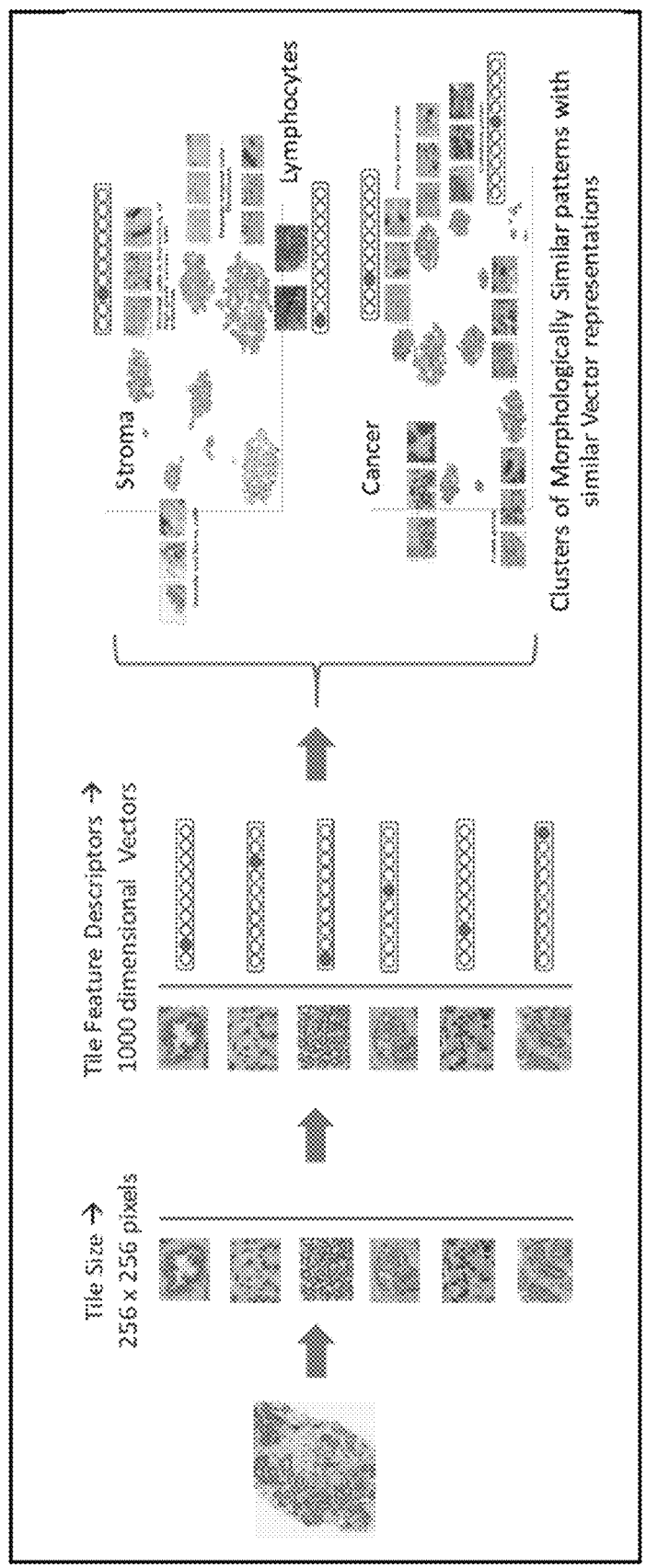
FIG. 1 illustrates a process of extraction, unsupervised vectorization and clustering of morphologically similar features.

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

Provided herein is a method to directly predict molecular changes, such as gene mutations, copy number variations, gene fusions, amplifications and deletions, from the morphometric analysis of H&E-stained tissue section images. In one embodiment, the method is carried out in a completely unsupervised manner, without prior knowledge of which patterns are reflective of the underlying molecular change. This is done on molecular markers that are already known to be predictive of tumor response in nature, but their correlation with distinct morphological features has not previously been ascertained. Molecular markers include, but are not limited to, PTEN, TMPRSS2-ERG, TP53, PIK3CA, MYC and ERBB2.

In another embodiment, provided herein is a method, which goes beyond known markers to directly predict patient outcome, and identify Regions of Interest (ROI) that are predictive of disease outcome in nature (as described herein). Molecular analysis of these ROIs shows proteogenomic markers that are uniquely expressed in the ROIs as compared to the rest of the tissues. These identified ROIs on the tissue sections are predictive, and relevant to performing molecular analysis to identify predictive biomarkers of patient response. The identification of aberrant genes/proteins present in the ROIs, which are responsible for causing the particular morphological changes of the ROIs, enables understanding and identification of mechanism/pathways responsible for therapy response prediction that are specific and easier than those found by proteogenomic analysis of the whole tissue, where the abnormality could be masked by the large preponderance of cells with normal proteogenomic patterns.

1. Feature Extraction→Unsupervised Vectorization and Clustering of Morphologically Similar Features Referring to FIG. 1, the figure illustrates a process of extraction, unsupervised vectorization and clustering of morphologically similar features. The system takes in as input a set of patients, with known molecular status. The dataset includes both patients with gene modification (mutation, CNV, fusion) or gene intact. The following steps are performed:

For each patient, the H&E WSIs are taken and broken up into patches of size 256×256 at 40× resolution.

A 1000-dimensional vector representation of the patch is generated.

The vectors are clustered to identify multiple sub-patterns for each label. This generates 100s of clusters of morphologically similar patterns that do not have an explicit label, but represent a phenotype.

This process converts unstructured data of gigapixel WSIs to a structure of clusters of morphological patterns. This structured representation of morphology enables downstream tasks of ranking these patterns and identify which patterns predict the gene modification.

1. Outcome Specific Feature Ranking→Optimized to Classify Between Two Patient Cohorts with Different Gene Status or Treatment Outcome For each patient, all the patches and corresponding vector representations for all the slides are collected. To capture the microenvironment of each patch, a N×N region is selected around each patch, and the vectors are averaged to generate a mean vector for each region.

The mean vectors are clustered per label to generate multiple clusters—this converts the 50-100 k patches into 100-200 distinct morphological clusters. K numbers of patched are now sampled uniformly across each cluster to generate a batch of vectors that represent the patient slides.

Each of the K patches are now converted to a score between 0 and 1, based on gene status. A high score (around 1) represents that the patch shows up in patients with gene modification, while a low score (around 0) represents gene intact. These scores are generated using a set of weights that are learned by the outcome based on known patient gene status or treatment outcome as labels.

The top and bottom R patches are selected and are combined to generate an outcome morphometric score for the patient. This forces the model to learn the most predictive features and give them the highest or lowest scores.

The model is further fine-tuned using a mistakes pipeline—patches are identified that are causing mispredictions, for example patches in non-recurrent patients that have a high score. These patches are collected, and training data is generated to fine-tune the predictions.

Based on patch level scores, Regions Of Interest (ROIs) are identified on the tissue slide that are predictive of the outcome.

Figures 3, 4:
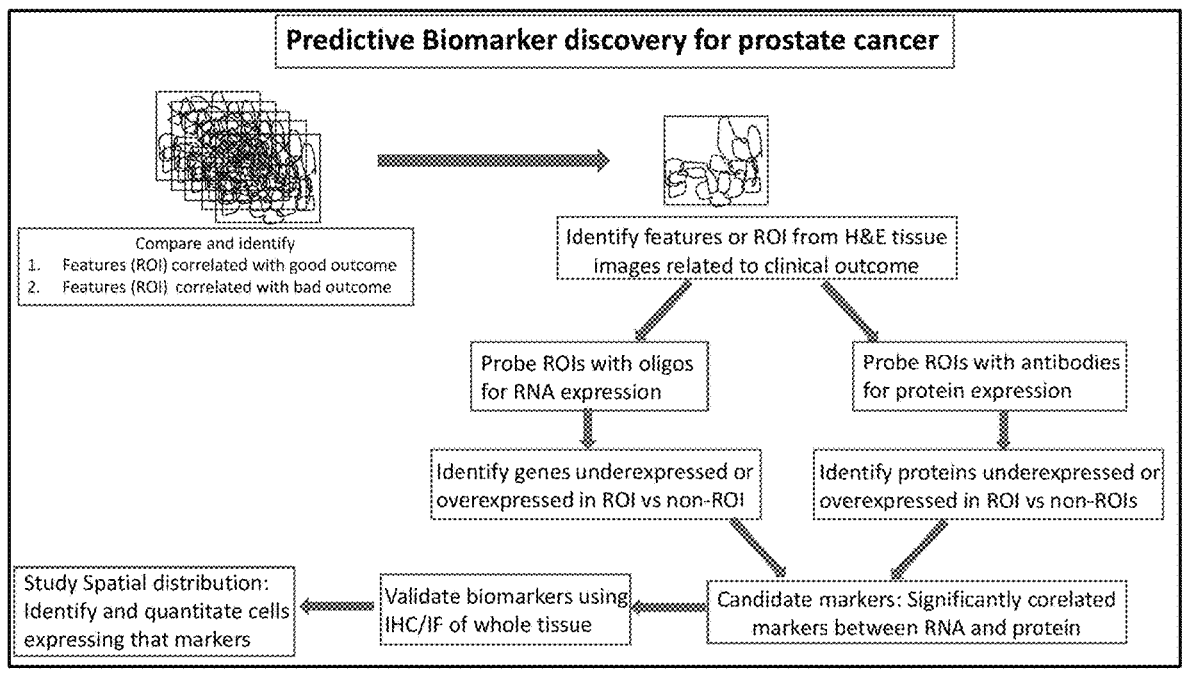
FIG. 3 illustrates a table showing prediction of gene mutations/copy number variations (CNVs) performed directly from H&E slides.
FIG. 4 illustrates a workflow for identification and quantitation of predictive biomarkers.

2. Prediction of Gene Mutations/Copy Number Variations (CNVs) Directly from H&E Slides Referring to FIG. 3, the figure illustrates a table showing results for prediction of gene mutations/copy number variations (CNVs) performed directly from H&E slides. Using the methods detailed above, we demonstrate 70-80% accuracy in predicting a range of gene modifications (mutation, fusion, amplification/deletion) across a range of tumor types (prostate, breast).

3. Workflow for Identification and Quantitation of Predictive Biomarkers

We first used targeted panel (total 140) of genes and proteins (80 oligonucleotides for specific RNA and 60 antibodies for specific proteins) that are known to be involved in response to multiple cancer therapy drugs and that includes among other proteins several immune markers to identify immune cells present in those ROIs, oncogenes and tumor suppressor genes involved in cancer growth and progression and present in those ROIs correlated with a disease/therapy outcome.

To identify the biomarker present in ROIs correlated with disease/therapy outcome, we used first Radical Prostatectomy tissue samples from prostate cancer patients, who recurred after 3 years of surgery. Using our AI platform, we have discovered novel and previously "unknown" morphological features from the tissue that drive tumor progression. We have trained the platform on several tens of millions of morphological examples of prostate cancer. The platform converts image patches into mathematical vector representations to generate hundreds of clusters of morphologically similar patterns using state-of-the-art Deep Convolutional Neural Network (CNN)-based models. This analysis provides information beyond traditional histopathological diagnosis by identifying patterns and features that capture tumor heterogeneity, and the stromal and TME components that are not easily distinguished and recognized by human eyes. This enables downstream tasks of ranking these patterns and identify specific patterns, which have high (and low) prognostic/predictive values. The model then ranks these image clusters based on patient outcome to identify novel Regions of Interest (ROIs). A high score (around 1) will represent the tile that will show up mainly in patients with adverse outcome, while a low score (around 0) will represent a good outcome. The tile level scores are combined to a slide level morphometric score to predict patient disease outcome. Differential proteogenomic analysis between High Scoring and Low Scoring ROIs results in discovery of novel proteogenomic biomarkers that drive tumor progression.

The ROIs are ranked high to low by AI models based on their presence related to the probability of fast progressing tumors, where RED represents higher probability of progression and YELLOW represents the relatively lower probability of progression within 3 years of RP. Once we identified several (12-24) ROIs that include cancer regions, stromal regions and regions that contained immune cells, we probe them with targeted panel of RNA probes and panel of antibodies against specific proteins and identified and quantitated RNA and protein expressed in those specific ROIs using methods described in https://pubmed.ncbi.nlm.nih-.gov/33303696/ We then performed correlation analysis of RNA versus protein expressed in those ROIs representing high probability of tumor progression and if there is a significant correlation found in RNA and protein of that particular biomarker expression, we considered that particular biomarker is present/expressed at a certain level as indicated by their quantitative value.

Using this methodology, we found high density levels of CD8, CD20, CD163 immune cells in tumor and high-density levels of CD4 and CD68 immune cells in tumor stroma, specific for cytotoxic T-cell, B-cell, Macrophages, M1 macrophages marker, cancer stem cell and MHC class II markers respectively are highly expressed in high scoring ROIs containing immune cells than compared to low scoring ROIs. In addition, we have also found high percentage of PDL1 and STING pathway proteins such as TMEM to be highly expressed in Immune and cancer cells in the high scoring ROIs indicating involvement of STING pathway in cancer recurrence. The relative protein and RNA expression levels and correlation therein is captured in FIGS. 5-7.

After screening of targeted panel of RNA and proteins for identification of highly expressed genes/protein in the ROIs, we performed immunohistochemical (IHC) or immunofluorescence (IF) analysis of the identified biomarkers including cancer markers Ki67, PTEN, AR, CC3, on whole slide tissue section. The IHC/IF biomarker slides can be generated for the protein markers identified in the ROIs to capture their spatial distribution in the TME. Higher percentage of PCa markers Ki67 identified and AR overexpressed and tumor suppressor PTEN is under-expressed in the higher scoring Red ROIs as compared to the lower scoring yellow ROIs and non-ROIs further establishing the validity of the method of ROI identification (as described herein). Each recurring patient image showed relatively higher percentage of the proteins Ki67 index (% of proliferating cells), higher immune marker PD-L1 expression, higher percentage of STING pathway proteins such as TMEM to be highly expressed and higher density of CD20, CD163 in tumor stroma and CD8+ T-cells both in epithelial and stromal areas in the ROIs and tumor core (PCa) relative to other tissues that are less predictive of disease progression. These biomarker slides can be co-registered with the H&E slides (or other types of input images, if available) to determine patch-level biomarker quantification and distribution, as well as other prognostic or predictive data. The combination of biomarker expression (quantitative) with morphology data can be used to further improve the accuracy of patient outcome prediction. IHC/IF study not only confirmed the expression of the above-mentioned specific biomarkers, but also identified and quantitated spatial distribution of these proteins. Identification, distributions and quantitation of types of immune cells or oncogenes and tumor suppressor genes present in their spatial context further predict the therapy response/outcome.

The ROIs can also be used as an input to a spatial profiling and biomarker identification where molecular analysis is to be performed. The molecular analysis is performed on the ROIs to capture differential expression of proteins/RNA in the regions marked as ROI versus regions not marked as ROI. The correlation is done on the ROIs versus the non-ROIs of patients with adverse outcome, as well as between patients with favorable outcomes to identify the protein/RNA markers that are driving the patient outcome.

EXAMPLES

Example 1: Feature Extraction, Unsupervised Vectorization and Clustering of Morphologically Similar Features The system takes in as input a set of subjects with known molecular status. The dataset includes subjects with one or more gene modifications due to mutations, copy-number variations (CNV), or fusion, and subjects with intact genes (as depicted in FIG. 1). The following steps are performed:

For each subject, hematoxylin and eosin (H&E) whole-slide images (WSIs) are taken and broken up into patches of size 256×256 pixel at 40× resolution.

A 1000 dimensional vector representation of the patch is generated.

The vectors are clustered to identify multiple sub-patterns for each label. This generates hundreds of clusters of morphologically similar patterns that do not have an explicit label, but represent a phenotype.

This process converts unstructured data of gigapixel WSIs to a structure of clusters of morphological patterns. This structured representation of morphology enables downstream tasks of ranking these patterns and identify which patterns predict the gene modification.

Figure 2:
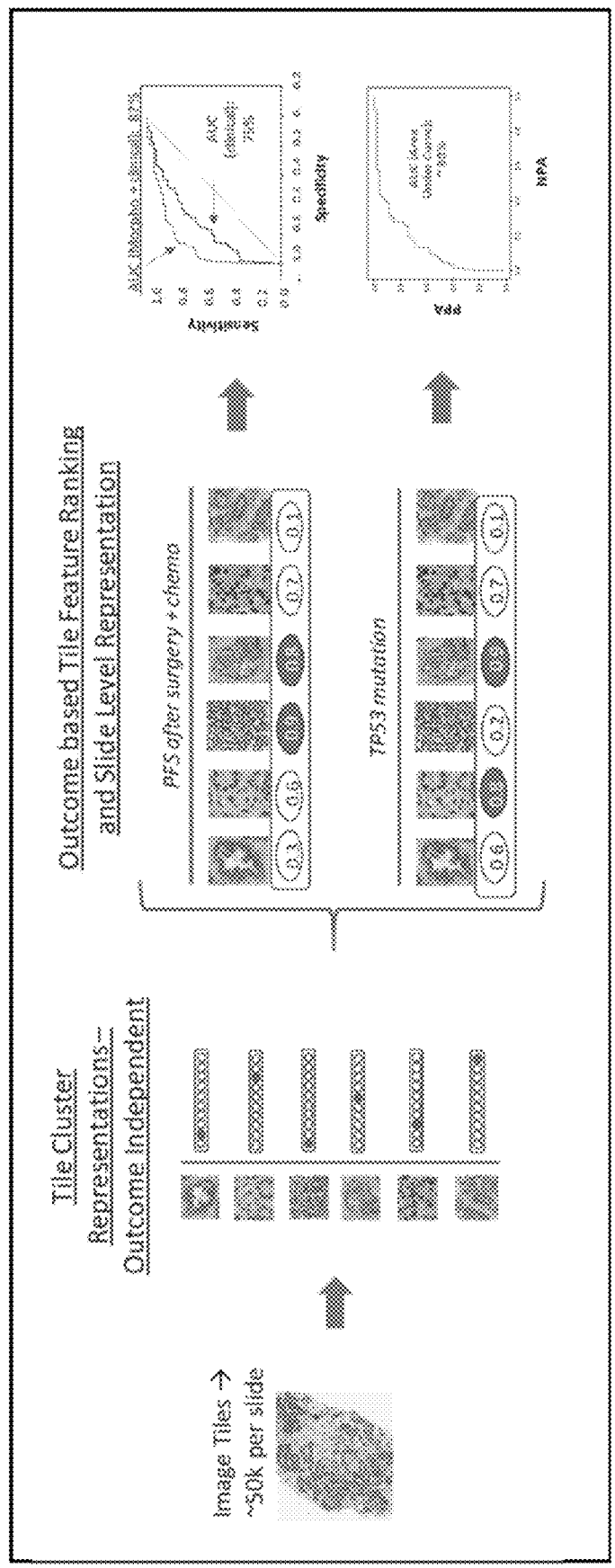
FIG. 2 illustrates an outcome specific feature ranking optimized to classify between two subject cohorts with different outcomes.

Example 2: Outcome Specific Feature Ranking Optimized to Classify Between Two Patient Cohorts with Different Gene Status or Treatment Outcome Referring to FIG. 2, the figure illustrates an outcome specific feature ranking optimized to classify between two subject cohorts with different outcomes. The following steps are performed as described in FIG. 2:

For each subject, all patches and corresponding vector representations for all the slides are collected. To capture the microenvironment of each patch, a N×N region is selected around each patch, and the vectors are averaged to generate a mean vector for each region.

The mean vectors are clustered per label to generate multiple clusters—this converts the 50-100 k patches into 100-200 distinct morphological clusters. K numbers of patches are now sampled uniformly across each cluster to generate a batch of vectors that represent the subject slides.

Each of the K patches is then converted to a score between 0 and 1, based on gene status. A high score (about 1) indicates that the patch shows up in subjects with gene modification. A low score (about 0) indicates the presence of intact genes. These scores are generated using a set of weights that are learned by the outcome based on known subject gene status or treatment outcome as labels.

The top and bottom R patches are selected and are combined to generate an outcome morphometric score for the subject. This forces the model to learn the most predictive features and give them the highest or lowest scores.

The model is further fine-tuned using a mistakes pipeline—patches are identified that are causing miss-predictions, for example, patches in non-recurrent subjects that have a high score. These patches are collected, and training data is generated to fine-tune the predictions.

Based on patch level scores, Regions Of Interest (ROIs) are identified on the tissue slide that are predictive of the outcome.

Example 3: Prediction of Gene Mutations/Copy Number Variations (CNVs) Directly from H&E Slides Referring to FIG. 3, the figure illustrates a table showing results for prediction of gene mutations/copy number variations (CNVs) performed directly from H&E slides. The results obtained from the methodology detailed above, shown in FIG. 3, demonstrate 70-80% accuracy in predicting a range of gene modifications due to mutation, fusion, amplification or deletions across a range of tumor types, such as prostate and breast cancers.

Example 4: Workflow for Identification and Quantitation of Predictive Biomarkers 140 targeted panels of genes and proteins (80 oligonucleotides for specific RNA and 60 antibodies for specific proteins) that are known to be involved in response to immunotherapy and multiple other cancer therapy drugs were used. These panels included several immune markers to identify immune cells present in ROIs, oncogenes and tumor suppressors involved in cancer growth and progression and correlated with a disease/therapy outcome.

To identify the biomarkers, present in ROIs, first radical prostatectomy tissue samples from prostate cancer subjects who recurred after 3 years of surgery, were used. Morphological features in ROIs, which correlated with disease outcome, in this case recurrence, were first identified using proprietary AI platform. Once several (12-24) ROIs that included cancer regions, stromal regions and regions that contained immune cells were identified, these ROIs were probed with targeted panels of RNA probes and panels of antibodies against specific proteins, and RNA and genes and protein expressed in those specific ROIs were identified and quantitated. The panel of RNA/Protein is listed in the table of FIG. 9. A correlation analysis of the RNA and proteins expressed in these ROIs was then performed. A significant correlation between RNA and proteins for a particular biomarker indicated presence or expression of the particular biomarker at a level defined by quantitative value.

The results, shown in FIGS. 5A-7, indicated high RNA and protein expression of CD8, CD20, CD68, CD163, CD44 and HLA-DR markers specific for cytotoxic T-cell, B-cell, macrophages, M1 macrophages marker, cancer stem cell and MHC class II markers, respectively, in ROIs containing immune cells that correspond to ROIs containing cancer and stromal cells.

Figure 5A:
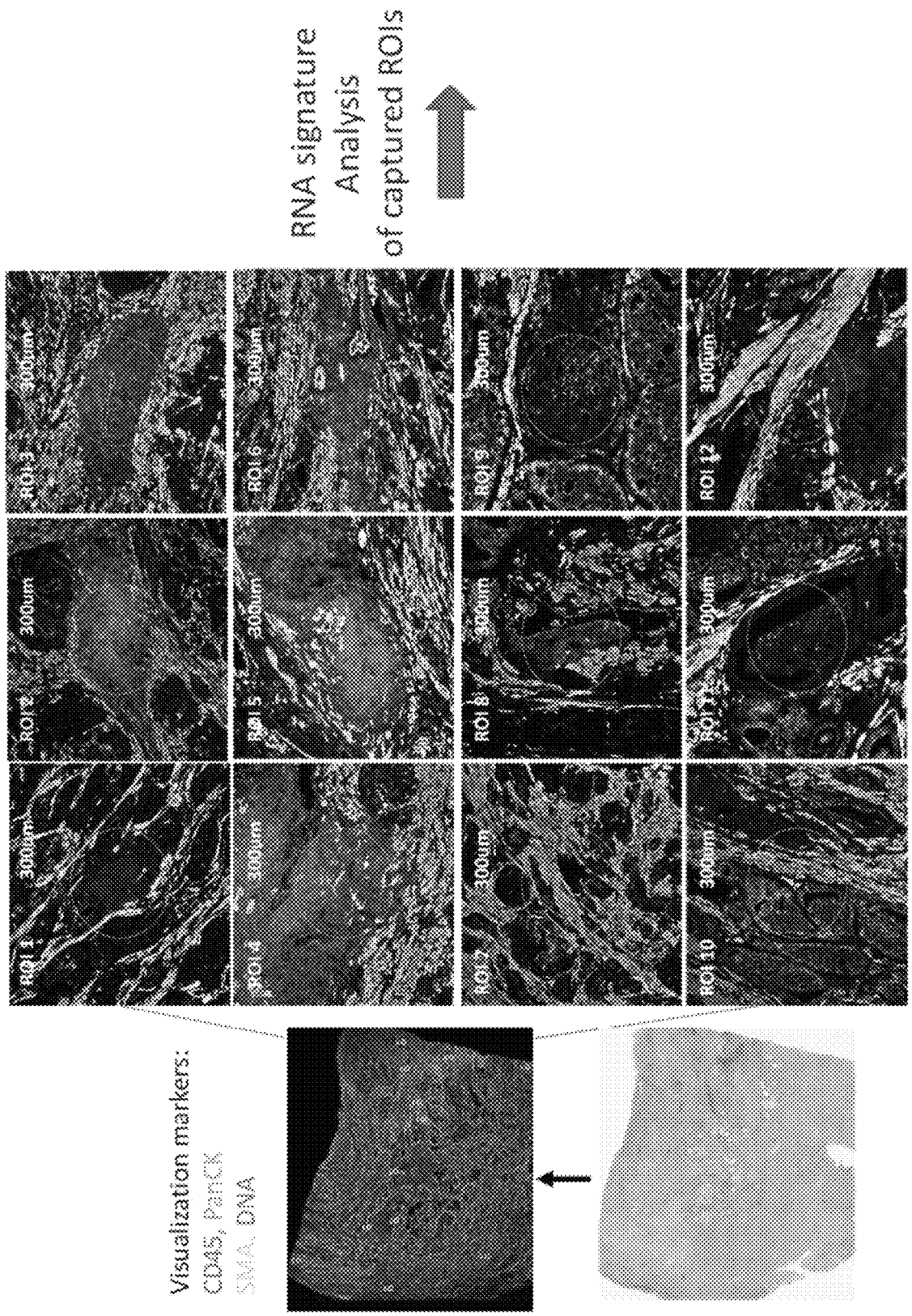
FIGS. 5A-5B illustrates a diagram showing spatial RNA expression of targeted gene panels in ROI of recurred prostate cancer samples. Mechanistic pathways of therapy response based on RNA signature in ROIs are identified.

FIG. 5A illustrates the Regions of Interest that were identified for RNA analysis—the ROIs include cancer, stromal and immune regions. These ROIs were probed with targeted panels of RNA probes, and the RNA expressed in those ROIs was quantified.

Figure 5B:
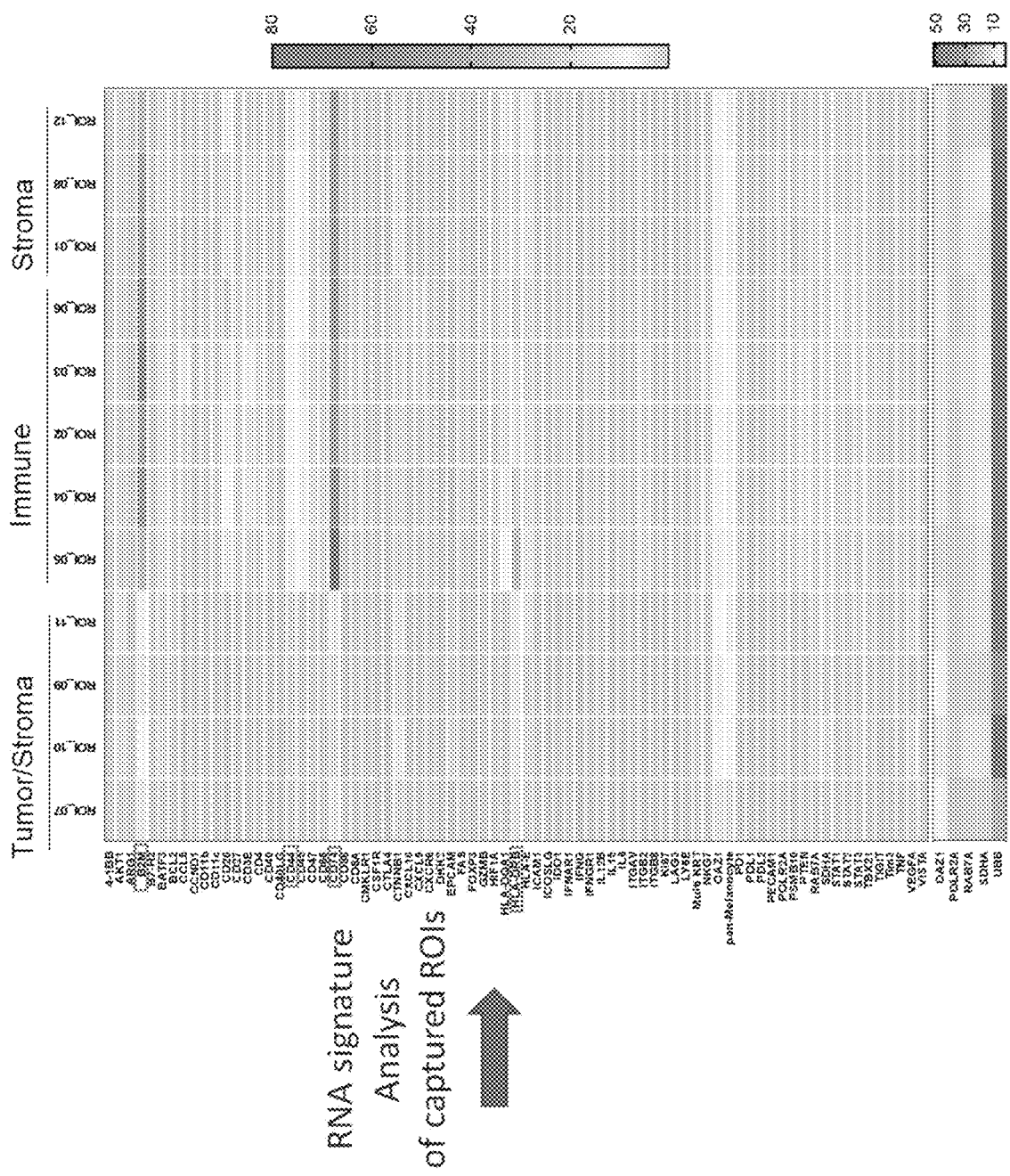

FIG. 5B illustrates the relative RNA expression of a panel of specific genes that are known to be involved in response to immunotherapy and multiple other targeted drugs. The expression level is categorized from Red to Blue, where Red represents relatively high expression, while Blue represents relative low expression.

Figure 6A:
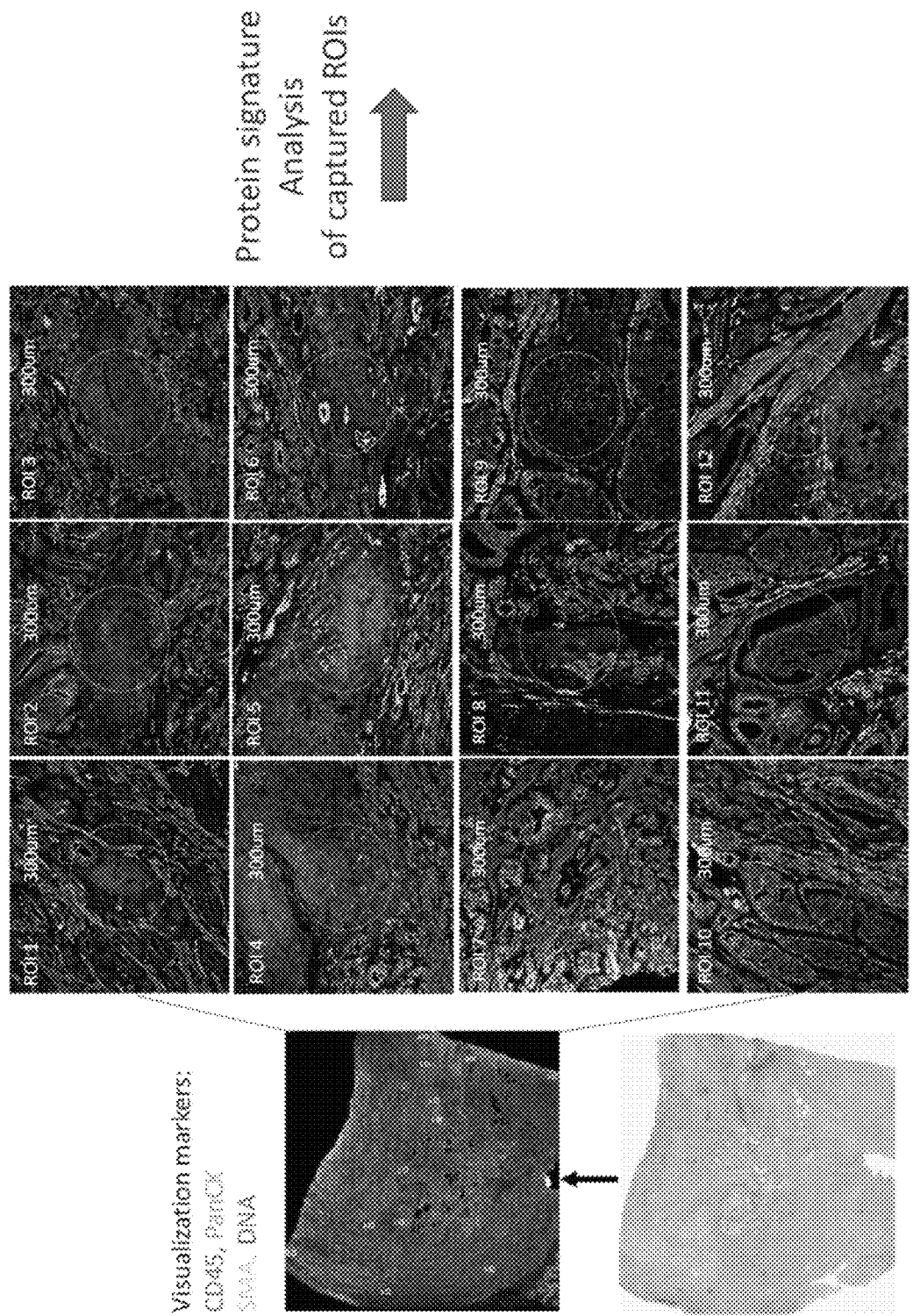
FIGS. 6A-6B illustrates a diagram showing spatial highplex protein expression in ROI of recurred prostate cancer samples. Mechanistic pathways of therapy response based on protein signature in ROIs are identified.

FIG. 6A illustrates the Regions of Interest that were identified for protein analysis—the ROIs include cancer, stromal and immune regions. These ROIs were the same as the ones used for RNA analysis, and were probed with targeted panels of antibodies, and the proteins expressed in those ROIs was quantified.

Figure 6B:
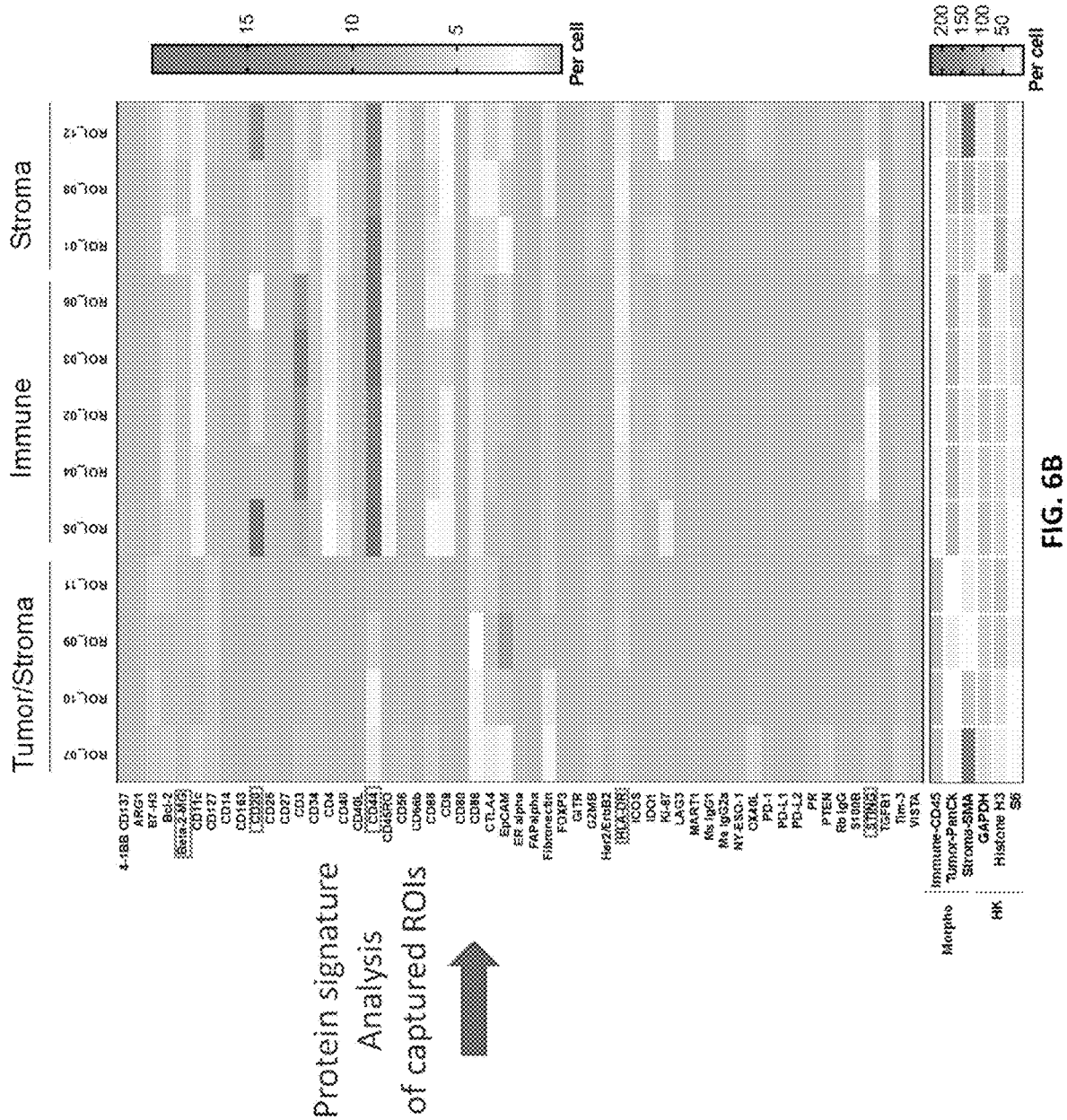

FIG. 6B illustrates the relative protein expression of a targeted panel of proteins that are known to be involved in response to immunotherapy and multiple other targeted drugs. The expression level is categorized from Red to Blue, where Red represents relatively high expression, while Blue represents relative low expression.

Figure 7:
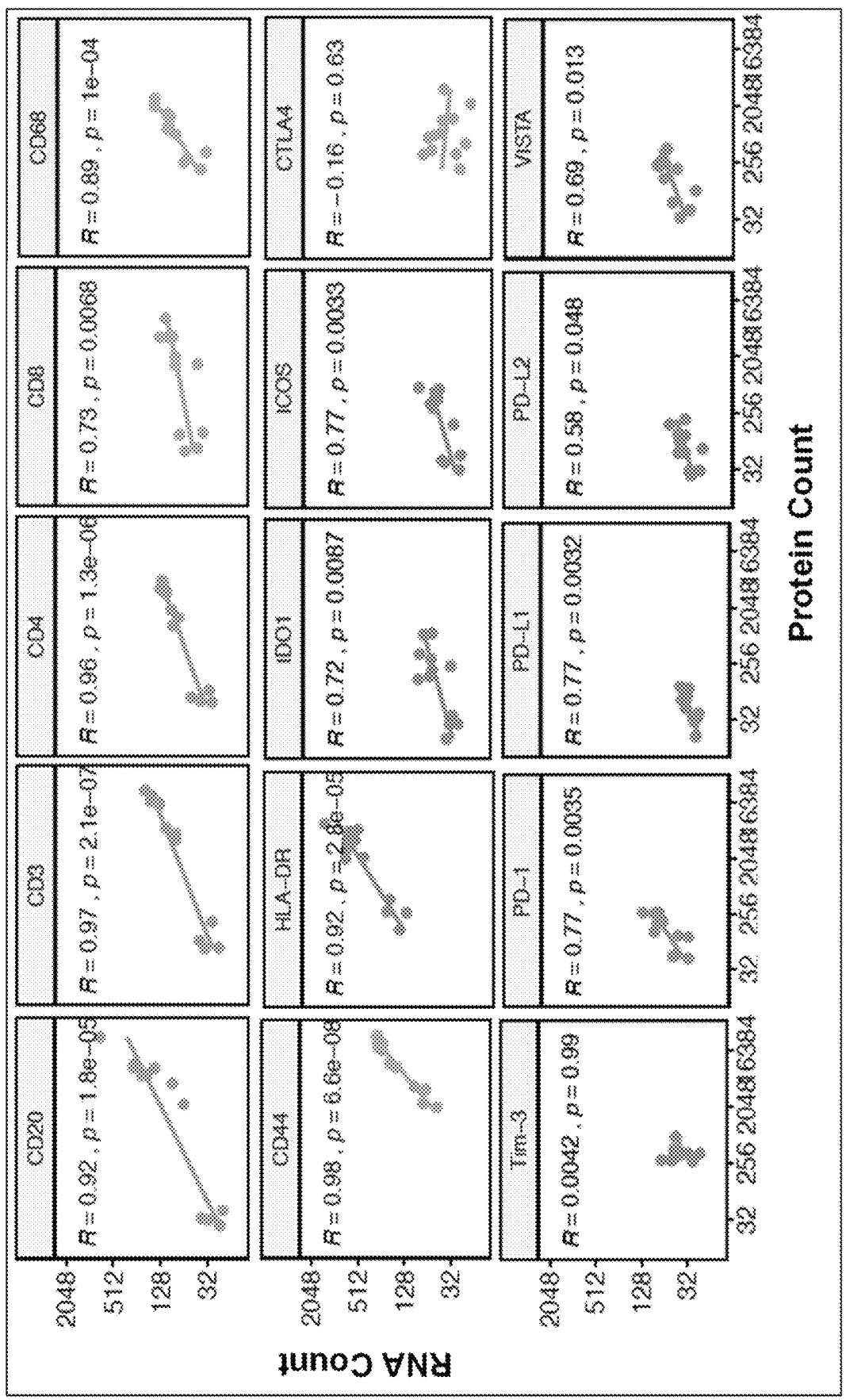
FIG. 7 illustrates a correlation between protein and RNA expression in recurred prostate cancer samples. Several proteins that are known to be related to tumor progression were identified.

FIG. 7 illustrates the correlation between the relative RNA and protein expression level for the same genes. When the correlation is high as is the case with CD20, CD3, CD4, HLA-DR, PD-L1 etc., it gives confidence that the data of measured RNA and protein expression is reliable and can be used to derive conclusions.

The results also showed STING pathway proteins such as TMEM to be highly expressed in Immune and cancer cells in the ROIs indicating involvement of STING pathway in cancer recurrence. The ROIs also indicated high density levels of CD8, CD20, CD163 immune cells in tumor and high density levels of CD4, CD68 immune cells in tumor stroma, and high percentage of immune cell markers PDL1 and STING pathway proteins/genes in cancer recurrence.

Following screening of targeted panel of RNA and proteins for identification of highly expressed genes/protein in the ROIs, immunohistochemical (IHC) and/or immunofluorescence (IF) analyses of the identified biomarkers were performed on whole slide tissue sections, and IHC/IF biomarker slides were generated for the protein markers identified in the ROIs to capture their spatial distribution in the tumor microenvironment. Higher percentage of Ki67 index (% of proliferating cells) was identified and AR was overexpressed while CC3 and tumor suppressor protein PTEN are under-expressed in the higher scoring Red ROIs as compared to the lower scoring yellow ROIs and non-ROIs. PCa cancer tissue (image) from each recurring patient image showed relatively higher percentage of Ki-67 index, higher immune marker PD-L1 expression PD-L1, higher percentage of STING pathway proteins such as TMEM to be highly expressed and higher density of CD20, CD163 in tumor stroma and CD8+ T-cells both in epithelial and stromal areas in the ROIs and tumor core (PCa) relative to other tissues that are less predictive of disease progression.

These biomarker slides can be co-registered with the H&E slides (or other types of input images, if available) to determine patch-level biomarker quantification and distribution, as well as other prognostic or predictive data. The combination of biomarker expression (quantitative) with morphology data can be used to further improve the accuracy of patient outcome prediction. IHC/IF study not only confirmed the expression of the above-mentioned specific biomarkers, but is also able to identify and quantitate spatial distribution of these proteins. Identification, distributions and quantitation of types of immune cells or oncogenes and tumor suppressor genes present in their spatial context help us further predict the therapy response/outcome.

Immunohistochemistry

One representative unstained tissue section containing PCa was selected by the pathologist from each prostatectomy (total 20 cases). Automated multiplex immunohistochemistry (IHC) was performed in the Pathology TRIP Laboratory at UW. PCa biomarkers (PTEN, AR, PSA, Ki-67 and cleaved caspase-3) and immune cells (CD4, CD8, CD20, CD68, CD163 and CD57) were detected and analyzed. PSMA was used as prostate epithelial mask for imaging analysis. The antibody information is listed in the table illustrated in FIG. 8. IHC was performed on the Ventana Discovery Ultra BioMarker Platform. Deparaffinization was carried out on the instrument, as was heat-induced epitope retrieval in the form of "cell conditioning" with CC1 buffer (Ventana #950-224), a tris-based buffer (pH 8.5), for approximately 56 minutes at 95° C. The combination of multiplexed immunostaining is as follows:

PSMA (HRP-DAB)+PTEN (AP-Red)+Ki67 (HRP-Purple)
PSA (HRP-DAB)+AR (AP-Red)+CC3 (HRP-Purple)
CD4 (HRP-DAB)+CD8 (AP-Red)+PSMA (HRP-purple)
NK1 (CD57) (DAB)+CD20 (HRP-Purple)+PSMA (HRP-purple)
CD68 (HRP-DAB)+CD163 (AP-Red)+PSMA (HRP-purple)
CTLA-4 (HRP-DAB)+PD-L1 (AP-red)+PSMA (HRP-Purple)
CD74 (DAB)+TMEM (STING) (red)+PSMA (HRP-purple)

Referring to FIG. 8, an example table listing Antibody information, including the Antibody name, the vender, catalog number and clone and dilution specifications is provided.

Biomarker Analysis

Referring to FIG. 10, the figure illustrates an example table describing a biomarker panel for tumor progression prediction. The stained slides were scanned with Leica Biosystems Aperio AT2 scanner in the TRIP Lab at UW. Halo software modules (Tissue Classifier, Multiplex IHC and Spatial Analysis, Indica Labs) were used for biomarker analysis. The pathologist with expertise in morphometric analysis performed the analysis. The positive thresholds for biomarkers were carefully determined by assessing the background and true signals for each biomarker using the software in the context of tissue morphology and biomarker cellular and subcellular distribution. Briefly, the background staining for each biomarker was determined by examining the average signal intensity carefully in a selected representative tissue area that the biomarker has been known to be not expressed, and a mean optical density (OD) value was obtained. This mean OD value plus 2 folds of standard deviation (SD) was used as the presumptive baseline threshold. This presumptive threshold was then fine-tuned by testing a few representative areas by an experienced pathologist to achieve a final background threshold for contrast to estimate the amount of the target proteins.

Using 7 cancer and immune markers (Ki67, CC3, AR, PTEN, TMEM, PDL1, CD74) and 5 Immune cells markers (CD8, CD4, CD20, CD68, C163, CD57) we obtained a set of 54 biomarkers highlighted for each of the 20 patients from their Red/Yellow and PCa/Per regions of epithelial, stromal and total tumor areas.

For each marker in the 54 biomarker set, comparisons between groups (PCa-Red vs, PCa-Yellow ROIs, and PCa vs. PCa-Per) for univariate analysis were conducted using a paired t-test. The Benjamini-Hochberg method was used to control the false discovery rate (FDR) at <0.05. All reported p-values are two-sided and P<0.05 was used to define statistical significance. Statistical analyses were conducted using SAS software (SAS Institute, Cary NC), version 9.4.

From the p-values of the set of 54 biomarkers, 12 biomarkers that have p-value<0.005 were selected for multivariate analysis of these 12 biomarkers associated with clinical outcome of time to recurrence post RP for the determination of the recurrence prediction score. For of the 12 markers selected from univariate analysis, the log-transformed ratio of Pca/Periphery ("red"/"yellow" ROI) was calculated. Multivariate linear regression analysis using Cox proportional regression modelling was conducted to evaluate the associations between the 12 markers and Time to recurrence post RP. (clinical outcome). In this analysis, Time from Prostatectomy. to Recurrence. was log-transformed. Backward variables selection (p<0.05) was used to identify a parsimonious model with significant predictors. The results of the backward selection procedure were confirmed using forward selection variable selection. The final parsimonious model with significant predictors (p<0.05) is shown in the table. A total of 10 out of the 12 markers remained in the final model with significant predictive power. The adjusted R2 was 0.59 which indicates adequate model fit.

The regression coefficient for each marker of the parsimonious model was used to construct an overall risk score for time to recurrence. Receiver operating characteristics (ROC) curve analysis will be utilized to construct risk categories for predicting probabilities or recurrence at pre-specified time points (6, 12, 18, 24, 36 months). Model discrimination will be quantified by calculating the area under the receiver operating curve and the c-statistic. Cross-validation studies will be conducted for model calibration".

Referring to FIGS. 13, and 14, the tables illustrate multivariate analysis. For of the 12 markers, the log-transformed ratio of Pca/Periphery ("red"/"yellow" ROI) was calculated. Multivariate linear regression analysis was conducted to evaluate the associations between the 12 markers and Time from Prost. to Rec. (clinical outcome). In this analysis, Time from Prost. to Rec. was log-transformed. Backward variables selection (p<0.05) was used to identify a parsimonious model with significant predictors. The results of the backward selection procedure was confirmed using forward selection variable selection. The final parsimonious model with significant predictors (p<0.05) is shown below. A total of 10 out of the 12 markers remained in the final model.

Multivariate analysis of these 12 biomarkers identified 10 biomarkers that were used to arrive at a scoring system to stratify patients according to their probability of tumor progression. For of the 12 markers, the log-transformed ratio of Pca/Periphery ("red"/"yellow" ROI) was calculated. Multivariate linear regression analysis was conducted to evaluate the associations between the 12 markers and Time from Prost. to Rec. (clinical outcome). In this analysis, Time from Prostatectomy. to Recurrence. was log-transformed. Backward variables selection (p<0.05) was used to identify a parsimonious model with significant predictors. The results of the backward selection procedure were confirmed using forward selection variable selection. The final parsimonious model with significant predictors (p<0.05) is shown in the table. A total of 10 out of the 12 markers remained in the final model with significant predictive power as shown in the table. The adjusted R2 was 0.59 which indicates adequate model fit.

Figure 11:
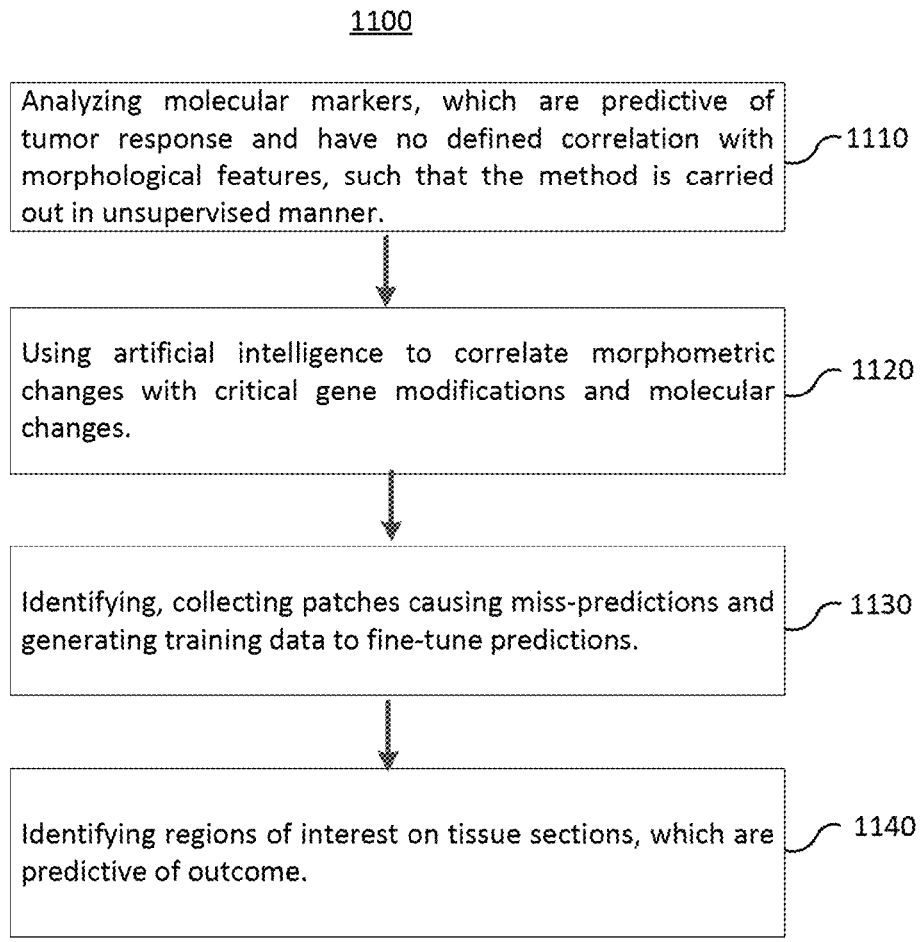
FIG. 11 illustrates an example method an embodiment described herein.

Referring to FIG. 11 illustrates an example method of an embodiment described herein. The system may perform the operations of analyzing molecular markers, which are predictive of tumor response and have no defined correlation with morphological features, such that the method is carried out in unsupervised manner (Step 1110). The system may use artificial intelligence to correlate morphometric changes with critical gene modifications and molecular changes (Step 1120). The system may perform operations of identifying, collecting patches causing miss-predictions and generating training data to fine-tune predictions (Step 1130). The system may perform the operation of identifying regions of interest on tissue sections, which are predictive of outcome (Step 1140).

Further Exemplary Embodiments

Example 1. A method of directly predicting molecular changes in one or more disease tissue sections from a subject, wherein the method comprises of (a) analyzing molecular markers, which are predictive of tumor response and have no defined correlation with morphological features, such that the method is carried out in unsupervised manner; and (b) using artificial intelligence to correlate morphometric changes with critical gene modifications and molecular changes.

Example 2. The method of example 1, wherein using artificial intelligence comprises (i) collecting whole-slide images (WSIs) of tissue sections obtained from the subject; (ii) feature extracting the whole-slide images into patches and corresponding vectors to generate clusters of vectors with morphologically similar patterns; (iii) sampling the patches uniformly across each cluster to generate a batch of vectors that represent the subject's images; (iv) generating a score between 0 and 1 for each patch based on gene status; and (v) generating an outcome morphometric score for the subject by combining selected patches.

Example 3. The method of example 2, wherein an N×N region is selected around each patch, and a mean vector is generated for each region.

Example 4. The method of example 3, wherein the molecular markers comprise of but not limited to PTEN, TMPRSS2-ERG, TP53, PIK3CA, MYC and ERBB2.

Example 5. The method of example 4, wherein extracted features are trained on multiple tumor types.

Example 6. The method of example 5, wherein tumor types comprise of but not limited to prostate, breast, gastrointestinal, ovary, liver and lung tumors.

Example 7. The method of example 6, wherein the tissue sections are stained with hematoxylin and eosin (H&E).

Example 8. The method of example 7, wherein molecular changes comprise one or more gene modifications selected from gene mutations, copy-number variations (CNV), gene amplifications, gene deletions and gene fusions.

Example 9. The method of example 8, wherein a score of 1 indicates a definite gene modification and a score of about 0 indicates a wild type gene.

Example 10. The method of example 9, wherein generating an outcome morphometric score for the subject indicates learning of predictive features.

Example 11. The method of example 10, wherein the method predicts a range of gene modifications across a range of tumor types with 70 to 90% accuracy.

Example 12. The method of example 11, wherein the method further comprises identifying, collecting patches causing miss-predictions and generating training data to fine-tune predictions.

Example 13. The method of example 12, wherein the method further comprises identifying regions of interest on tissue sections, which are predictive of outcome.

Example 14. A system for directly predicting molecular changes in one or more tissue sections from a subject, wherein the system is configured to (a) analyze molecular markers, which are predictive of tumor response and have no defined correlation with morphological features, such that the analysis is carried out in unsupervised manner; and (b) use artificial intelligence to correlate morphometric changes with critical gene modifications and molecular changes.

Example 15. The system of example 14, wherein the system is configured to (a) collect whole-slide images (WSIs) of tissue sections obtained from the subject; (b) feature extract the whole-slide images into patches and corresponding vectors to generate clusters of vectors with morphologically similar patterns; (c) sample the patches uniformly across each cluster to generate a batch of vectors that represent the subject's images; (d) generate a score between 0 and 1 for each patch based on gene status; and (e) generate an outcome morphometric score for the subject by combining selected patches.

Example 16. The system of example 15, wherein the system is configured to select an N×N region around each patch, and generate a mean vector for each region.

Example 17. The system of example 16, wherein the molecular markers comprise PTEN, TMPRSS2-ERG, TP53, PIK3CA, MYC and ERBB2.

Example 18. The system of example 17, wherein the system is trained on multiple tumor types.

Example 19. The system of example 18, wherein tumor types comprise of but not limited to prostate, breast, gastrointestinal, ovary, liver and lung tumors.

Example 20. The system of example 19, wherein the tissue sections are stained with hematoxylin and eosin (H&E).

Example 21. The system of example 20, wherein molecular changes comprise one or more gene modifications selected from gene mutations, copy-number variations (CNV), gene amplifications, gene deletions and gene fusions.

Example 22. The system of example 21, wherein a score of 1 indicates a definite gene modification and a score of about 0 indicates a wild type gene.

Example 23. The system of example 22, wherein generating an outcome morphometric score for the subject forces the system to learn predictive features.

Example 24. The system of example 23, wherein the system predicts a range of gene modifications across a range of tumor types with 70 to 90% accuracy.

Example 25. The system of example 24, wherein the system is further configured to identify and collect patches causing miss-predictions, and generate training data to fine-tune predictions.

Example 26. The system of example 25, wherein the system is further configured to identify regions of interest on tissue sections, which are predictive of outcome.

Example 27. A method for directly predicting an outcome of one or more subjects having a disease or at risk of developing a disease, and for identifying regions of interest that are predictive of disease outcome in one or more tissue sections from the subjects, wherein the method comprises (a) collecting whole-slide images (WSIs) of tissue sections obtained from one or more subjects; (b) identifying regions of interest (ROIs) corresponding to morphological features correlated with disease outcome; (c) probing the ROIs with RNA probes and antibody probes; (d) identifying and quantifying RNA and proteins expressed in the ROIs; (e) performing a correlation analysis between the RNA and the proteins expressed in the ROIs; and (f) identifying biomarkers in the ROIs which are not expressed or are more or less expressed in other areas of the tissues and in tissues from patients with favorable outcome, thereby identifying ROIs that are predictive of disease outcome and predicting the outcome of the one or more subjects.

Example 28. The method of example 27, wherein the tissue sections are stained with hematoxylin and eosin (H&E).

Example 29. The method of example 28, wherein the method further comprises of identifying mechanisms or pathways for therapy response specific to biomarker expression in the ROIs.

Example 30. The method of example 29, wherein the ROIs comprise of cancer regions, stromal regions and regions that contain immune cells.

Example 31. The method of example 30, wherein the biomarkers comprise of biomarkers specific for cytotoxic T cells, B cells, macrophages, M1 macrophages, cancer stem cells and MHC class II as well as cancer markers Ki67, CC3, PTEN and AR Example 32. The method of example 31, wherein the biomarkers comprise of but not limited to Ki67, CC3, PTEN, AR, CD8, CD4, CD20, CD68, CD163, CD44, CD74, CD57, PD-L1, PD-1, CTLA-4, HLA-DR, and STING pathway proteins such as TMEM.

Example 33. The method of example 32, wherein the method further comprises determining spatial distribution of identified biomarkers in tumor microenvironments by immunohistochemical (IHC) and/or immunofluorescence (IF) analysis on whole slide tissue sections.

Example 34. The method of example 33, wherein the method further comprises of combining quantitative biomarker expression in the ROIs with morphological data of the ROIs by co-registering IHC and/or IF whole slide tissue sections with hematoxylin and eosin (H&E) whole slide tissue sections to increase accuracy of prediction.

Example 35. A system for directly predicting an outcome of one or more subjects having a disease or at risk of developing a disease, and for identifying regions of interest that are predictive of disease outcome in one or more tissue sections from the subjects, wherein the system is configured to (a) collect whole-slide images (WSIs) of tissue sections obtained from one or more subjects; (b) identify regions of interest (ROIs) corresponding to morphological features correlated with disease outcome; (c) probe the ROIs with genes and protein specific probes; (d) identify and quantify RNA and proteins expressed in the ROIs; (e) perform a correlation analysis between the RNA and the proteins expressed in the ROIs; and (f) identify biomarkers in the ROIs which are not expressed or are more or less expressed in other tissues, thereby identifying ROIs that are predictive of disease outcome and predicting the outcome of the one or more subjects.

Example 36. The system of example 35, wherein the tissue sections are stained with hematoxylin and eosin (H&E).

Example 37. The system of example 36, wherein the system is further configured to identify mechanisms or pathways for therapy response specific to biomarker expression in the ROIs.

Example 38. The system of example 37, wherein the ROIs comprise cancer regions, stromal regions and regions that contain immune cells.

Example 39. The system of example 38, wherein the biomarkers comprise biomarkers specific for cytotoxic T cells, B cells, macrophages, M1 macrophages, cancer stem cells and MHC class II.

Example 40. The system of example 39, wherein the biomarkers comprise of but not limited to CD8, CD4, CD20, CD68, CD163, CD44, CD57, HLA-DR, PDL-1, PD-1, CD74, STING pathway proteins such as TMEM, Ki67, CC3, AR and PTEN.

Example 41. The system of example 40, wherein the system is further configured to perform immunohistochemical (IHC) and/or immunofluorescence (IF) analysis on whole slide tissue sections to determine spatial distribution of identified biomarkers in tumor microenvironments.

Example 42. The system of example 41, wherein the system is further configured to identify quantitative expression of 12 biomarker proteins Ki67, CC3, PD-L1, PTEN OD, STING pathway proteins such as TMEM OD, CD8, CD163 in ROIs and CD8, CD20, CD163, CD68 in Tumor each with univariate analysis had statistically significant variations between high scoring ROIs and lower scoring ROIs with p-values<0.05 as stated in Table 2, and are significantly either over or under-expressed in the ROIs as compared to the non-ROIs with the morphological data of the ROIs by co-registering IHC and/or IF whole slide tissue sections with hematoxylin and eosin (H&E) stained whole slide tissue sections, thereby increasing the accuracy of prediction of disease outcome.

Example 43. In one example, there is a system for directly predicting outcome of one or more subjects having disease or at risk of developing a disease and for identifying regions of interest that are predictive of disease outcome in or more tissue sections from the subjects, wherein the system is configured to: (a) collect whole-slide images (WSIs) of tissue sections obtained from one or more subjects; (b) identify regions of interest (ROIs) corresponding to morphological features correlated with disease outcome; (c) probe the ROIs with genes and protein specific probes; (d) identify and quantify RNA and proteins expressed in the ROIs; (e) perform a correlation analysis between the RNA and the proteins expressed in the ROIs; and (f) identify biomarkers in the ROIs which are not expressed or are more or less expressed in other tissues, thereby identifying ROIs that are predictive of disease outcome and predicting the outcome of the one or more subjects. In this example, the system may further comprise the operations of: (a) identifying and collecting patches from tissue sections for predicting regions of interest (ROIs) of tissue sections responsible for tumor progression; (b) performing an operation of univariate analysis conducted using a paired t-test for identifying 12 univariate markers from the ROIs responsible for tumor progression while the Benjamini-Hochberg method was used to control the false discovery rate (FDR) at <0.05 (where reported p-values are two-sided and P<0.05 was used to define statistical significance); and (c) performing an operation of multivariate linear regression analysis using Cox proportional regression modeling to identify a parsimonious model with statistical significant (p<0.05) and evaluate the associations between the 12 markers and Time to tumor progression (e.g., clinical outcome) to select a set of 10 of the 12 biomarkers with significant predictive power as shown in the table to derive a scoring system for stratifying patients according to their probability of tumor progression. A regression coefficient for each marker of the parsimonious model was used to construct an overall risk score for time to recurrence. Receiver operating characteristics (ROC) curve analysis may be utilized to construct risk categories for predicting probabilities or recurrence at pre-specified time points (6, 12, 18, 24 months). Model discrimination is quantified by calculating the area under the receiver operating curve and the c-statistic.

Example Computer System

Figure 12:
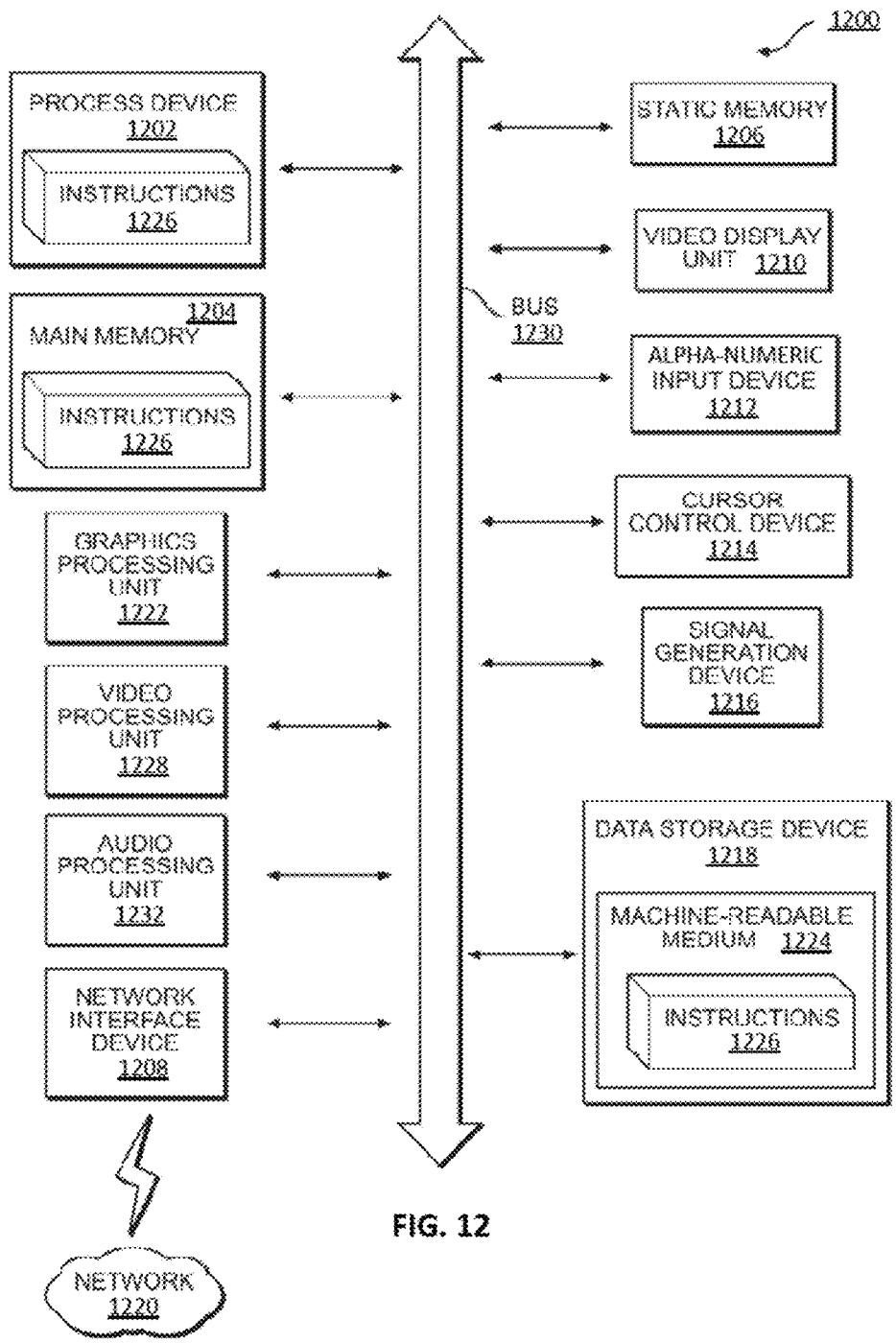
FIG. 12 illustrates a diagram of an exemplary environment in which some embodiments may operate

FIG. 12 illustrates an example machine of a computer system within which a set of instructions, for causing the machine to perform any one or more of the methodologies discussed herein, may be executed. In alternative implementations, the machine may be connected (e.g., networked) to other machines in a LAN, an intranet, an extranet, and/or the Internet. The machine may operate in the capacity of a server or a client machine in client-server network environment, as a peer machine in a peer-to-peer (or distributed) network environment, or as a server or a client machine in a cloud computing infrastructure or environment.

The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 1200 includes a processing device 1202, a main memory 1204 (e.g., read-only memory (ROM), flash memory, dynamic random access memory (DRAM) such as synchronous DRAM (SDRAM) or Rambus DRAM (RDRAM), etc.), a static memory 1206 (e.g., flash memory, static random access memory (SRAM), etc.), and a data storage device 1218, which communicate with each other via a bus 1230.

Processing device 1202 represents one or more general-purpose processing devices such as a microprocessor, a central processing unit, or the like. More particularly, the processing device may be a complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 802 may also be one or more special-purpose processing devices such as an application specific integrated circuit (ASIC), a field programmable gate array (FPGA), a digital signal processor (DSP), network processor, or the like. The processing device 1202 is configured to execute instructions 1226 for performing the operations and steps discussed herein.

The computer system 1200 may further include a network interface device 1208 to communicate over the network 1220. The computer system 1200 also may include a video display unit 1210 (e.g., a liquid crystal display (LCD) or a cathode ray tube (CRT)), an alphanumeric input device 1212 (e.g., a keyboard), a cursor control device 1214 (e.g., a mouse), a graphics processing unit 1222, a signal generation device 1216 (e.g., a speaker), graphics processing unit 1222, video processing unit 1228, and audio processing unit 1232.

The data storage device 818 may include a machine-readable storage medium 1224 (also known as a computer-readable medium) on which is stored one or more sets of instructions or software 1226 embodying any one or more of the methodologies or functions described herein. The instructions 1226 may also reside, completely or at least partially, within the main memory 1204 and/or within the processing device 1202 during execution thereof by the computer system 1200, the main memory 1204 and the processing device 1202 also constituting machine-readable storage media.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "determining" or "executing" or "performing" or "collecting" or "creating" or "sending" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMS, EEPROMs, magnetic or optical cards, or any type of media suitable for storing electronic instructions, each coupled to a computer system bus.

Various general purpose systems may be used with programs in accordance with the teachings herein, or it may prove convenient to construct a more specialized apparatus to perform the method. The structure for a variety of these systems will appear as set forth in the description above. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

In the foregoing disclosure, implementations of the disclosure have been described with reference to specific example implementations thereof. It will be evident that various modifications may be made thereto without departing from the broader spirit and scope of implementations of the disclosure as set forth in the following claims. The disclosure and drawings are, accordingly, to be regarded in an illustrative sense rather than a restrictive sense.

In the foregoing disclosure, implementations of the disclosure have been described with reference to specific example implementations thereof. It will be evident that various modifications may be made thereto without departing from the broader spirit and scope of implementations of the disclosure as set forth in the following claims. The disclosure and drawings are, accordingly, to be regarded in an illustrative sense rather than a restrictive sense.

What is claimed is:

1. A computer-implemented method of directly predicting molecular changes in one or more disease tissue sections from a subject, the method comprising:
   analyzing molecular markers, which are predictive of tumor response and have no defined correlation with morphological features, such that the method is carried out in unsupervised manner; and
   using artificial intelligence to correlate morphometric changes with critical gene modifications and molecular changes, wherein using the artificial intelligence comprises:
   (i) collecting whole-slide images (WSIs) of tissue sections obtained from the subject;
   (ii) feature extracting the whole-slide images into patches and corresponding vectors to generate clusters of vectors with morphologically similar patterns;
   (iii) sampling the patches uniformly across each cluster to generate a batch of vectors that represent the subject's images;
   (iv) generating a score between 0 and 1 for each patch based on gene status; and
   (v) generating an outcome morphometric score for the subject by combining selected patches;
   (vi) identifying regions of interest (ROIs) corresponding to morphological features correlated with disease outcome;
   (vii) probe the ROIs with genes and protein specific probes;
   (viii) identifying and quantifying RNA and proteins expressed in regions of interest (ROIs);
   (ix) performing a correlation analysis between the RNA and the proteins expressed in the ROIs; and
   (x) identifying biomarkers in the ROIs based on their expression or non-expression in other tissues, thereby identifying ROIs that are predictive of disease outcome.

2. The method of claim 1, wherein an N×N region is selected around each patch, and a mean vector is generated for each region.

3. The method of claim 1, wherein the molecular markers comprise PTEN, TMPRSS2-ERG, TP53, PIK3CA, MYC and ERBB2.

4. The method of claim 1, wherein extracted features are trained on multiple tumor types, and wherein tumor types comprise prostate, breast, gastrointestinal, ovary, liver and lung tumors.

5. The method of claim 1, wherein the tissue sections are stained with hematoxylin and eosin (H&E).

6. The method of claim 1, wherein molecular changes comprise one or more gene modifications selected from gene mutations, copy-number variations (CNV), gene amplifications, gene deletions and gene fusions.

7. The method of claim 1, wherein a score of 1 indicates a definite gene modification and a score of 0 indicates a wild type gene.

8. The method of claim 1, wherein generating an outcome morphometric score for the subject indicates learning of predictive features.

9. The method of claim 1, wherein the method predicts a range of gene modifications across a range of tumor types with 70 to 90% accuracy.

10. The method of claim 1, wherein the method further comprises:
  collecting patches causing miss-predictions and generating training data to fine-tune predictions; and
  identifying regions of interest on tissue sections, which are predictive of outcome.

11. A system comprising one or more processors, and a non-transitory computer-readable medium including one or more sequences of instructions that, when executed by the one or more processors, cause the system to perform operations comprising:
  analyzing molecular markers, which are predictive of tumor response and have no defined correlation with morphological features, such that the method is carried out in unsupervised manner; and
  using artificial intelligence to correlate morphometric changes with critical gene modifications and molecular changes, wherein using artificial intelligence comprises:
  (i) collecting whole-slide images (WSIs) of tissue sections obtained from the subject;
  (ii) feature extracting the whole-slide images into patches and corresponding vectors to generate clusters of vectors with morphologically similar patterns;
  (iii) sampling the patches uniformly across each cluster to generate a batch of vectors that represent the subject's images;
  (iv) generating a score between 0 and 1 for each patch based on gene status; and
  (v) generating an outcome morphometric score for the subject by combining selected patches;
  (vi) identifying regions of interest (ROIs) corresponding to morphological features correlated with disease outcome;
  (vii) probe the ROIs with genes and protein specific probes;
  (viii) identifying and quantifying RNA and proteins expressed in regions of interest (ROIs);
  (ix) performing a correlation analysis between the RNA and the proteins expressed in the ROIs; and
  (x) identifying biomarkers in the ROIs based on their expression or non-expression in other tissues, thereby identifying ROIs that are predictive of disease outcome.

12. The system of claim 11, wherein an N×N region is selected around each patch, and a mean vector is generated for each region.

13. The system of claim 11, wherein the molecular markers comprise PTEN, TMPRSS2-ERG, TP53, PIK3CA, MYC and ERBB2.

14. The system of claim 11, wherein extracted features are trained on multiple tumor types, and wherein tumor types comprise prostate, breast, gastrointestinal, ovary, liver and lung tumors.

15. The system of claim 11, wherein the tissue sections are stained with hematoxylin and eosin (H&E).

16. The system of claim 11, wherein molecular changes comprise one or more gene modifications selected from gene mutations, copy-number variations (CNV), gene amplifications, gene deletions and gene fusions.

17. The system of claim 11, wherein a score of 1 indicates a definite gene modification and a score of 0 indicates a wild type gene.

18. The system of claim 11, wherein generating an outcome morphometric score for the subject indicates learning of predictive features.

19. The system of claim 11, further comprising the operations of:
  predicting a range of gene modifications across a range of tumor types with 70 to 90% accuracy.

20. The system of claim 11, further comprising the operations of:
  collecting patches causing miss-predictions and generating training data to fine-tune predictions; and
  identifying regions of interest on tissue sections, which are predictive of outcome.

21. The system of claim 11, further comprising the operations of:
  identifying and collecting patches from tissue sections for predicting the ROIs of tissue sections responsible for tumor progression;
  performing univariate analysis using a paired t-test and the Benjamini-Hochberg method to control the false discovery rate (FDR) at <0.05 for identifying multiple univariate markers from the ROIs responsible for tumor progression;
  performing multivariate linear regression analysis using a Cox proportional regression modeling to evaluate the associations between the multiple markers and a time to tumor progression; and
  identifying a sub-set of the multiple markers according to a probability of tumor progression.

22. The system of claim 21, further comprising the operations of:
  constructing an overall risk score for time to recurrence based on a regression coefficient for each of the univariate markers.

* * * * *